United States Patent [19]

Yost et al.

[11] Patent Number: 5,114,439
[45] Date of Patent: May 19, 1992

[54] DIRECT RESISTIVE HEATING AND TEMPERATURE MEASUREMENT OF METAL-CLAD CAPILLARY COLUMNS IN GAS CHROMATOGRAPHY AND RELATED SEPARATION TECHNIQUES

[75] Inventors: Richard A. Yost; Mark E. Hail, both of Gainesville, Fla.

[73] Assignee: University of Florida, Gainesville, Fla.

[21] Appl. No.: 587,513

[22] Filed: Sep. 25, 1990

Related U.S. Application Data

[63] Continuation of Ser. No. 372,270, Jun. 27, 1989, abandoned.

[51] Int. Cl.⁵ .............................................. B01D 15/08
[52] U.S. Cl. .................................................. 55/20; 55/67; 55/197; 55/208; 55/386
[58] Field of Search .................. 55/20, 67, 197, 208, 55/267, 270, 386; 73/23.1; 219/490, 497, 501

[56] References Cited

U.S. PATENT DOCUMENTS

| | | | |
|---|---|---|---|
| 3,057,183 | 10/1962 | Deford | 55/197 X |
| 3,063,286 | 11/1962 | Nerheim | 55/386 X |
| 3,115,766 | 12/1963 | Winters | 73/23 |
| 3,225,520 | 12/1965 | Burow | 55/67 |
| 3,225,521 | 12/1965 | Burow | 55/67 |
| 3,232,093 | 2/1966 | Burow et al. | 73/23.1 |
| 3,514,925 | 6/1970 | Bossart | 55/386 |
| 3,624,986 | 12/1971 | Shoemake | 55/197 |
| 3,789,190 | 1/1974 | Orosy et al. | 219/497 |
| 3,831,555 | 8/1974 | Srinivas | 118/506 |
| 4,096,908 | 6/1978 | Lamy | 165/64 |
| 4,242,227 | 12/1980 | Lamparski et al. | |
| 4,350,586 | 9/1982 | Conlon et al. | 55/197 X |
| 4,376,641 | 3/1983 | Nestrick et al. | |
| 4,474,825 | 10/1984 | Schmidt | 427/10 |
| 4,523,084 | 6/1985 | Tamura et al. | 219/497 |
| 4,549,073 | 10/1985 | Tamura et al. | 219/497 |
| 4,554,436 | 11/1985 | Chlosta et al. | 55/386 X |
| 4,599,095 | 7/1986 | Barnes et al. | 55/208 |
| 4,642,154 | 2/1987 | Thalmann et al. | 219/490 X |
| 4,650,964 | 3/1987 | Vincent | 219/301 |
| 4,695,709 | 9/1987 | Sachs et al. | 219/494 |
| 4,721,846 | 1/1988 | Lupoli et al. | 55/208 X |
| 4,726,822 | 2/1988 | Cates et al. | 55/386 X |
| 4,728,776 | 3/1988 | Vincent | 219/301 |
| 4,735,259 | 4/1988 | Vincent | 165/47 |
| 4,805,441 | 2/1989 | Sides et al. | 55/67 X |

FOREIGN PATENT DOCUMENTS

| | | | |
|---|---|---|---|
| 636078 | 2/1962 | Canada | 55/386 |
| 61-265568 | 11/1986 | Japan | 55/386 |
| 61-288154 | 12/1986 | Japan | 55/386 |
| 82-01578 | 5/1982 | PCT Int'l Appl. | 55/386 |

OTHER PUBLICATIONS

Milton L. Lee et al., *Open Tubular Column Chromatography*, (a Wiley-Interscience Publication, John Wiley & Sons, 1984) Chapter 4, p. 110.

*Primary Examiner*—Robert Spitzer
*Attorney, Agent, or Firm*—Kerkam, Stowell, Kondracki & Clarke

[57] ABSTRACT

An improved system and method for high resolution gas chromatography (GC) is disclosed. This invention involves the use of fused silica open tubular capillary columns having a conductive exterior coating and an arrangement for electrically coupling a power source to such coating, whereby it is now possible to effect direct resistive heating of the capillary column while controlling the temperature thereof. Such control is achieved by measurement of the resistance of the conductive coating, correlating such resistance with the temperature of the column and increasing or decreasing the electrical power supplied to such coating, as appropriate, to effect the desired adjustment in column temperature. Because of the low thermal mass of the column and the conductive coating, temperature changes can be effected readily thereby improving the speed of such separation and reducing the time interval between resolution of successive samples. In the preferred embodiments of this invention, the system is incorporated in what is referred to as "short column" gas chromatography instrumentation and thus suitable for "non-selective" detection systems or selective detection methods. Because of the relative compact nature and low power demands of the system of this invention, such system can be operated as a portable unit.

15 Claims, 6 Drawing Sheets

DIRECT RESISTIVE HEATING AND TEMPERATURE MEASUREMENT OF METAL-CLAD CAPILLARY COLUMNS IN GAS CHROMATOGRAPHY AND RELATED SEPARATION TECHNIQUES

This application is a continuation of application Ser. No. 07/372.270 filed Jun. 27, 1989 now abandoned.

BACKGROUND OF THE INVENTION

1. Field of the Invention

This invention is directed to a system and to a method. More specifically, this invention relates to improvements in design and operation of gas chromatography instrumentation and improvements in gas chromatographic analysis techniques. This invention further provides an improvement in system and method for heating and temperature control of gas chromatography columns utilizing resistance heating and resistance measurements techniques. More specifically, the system and method of this invention permit direct resistive heating involving the use of fused silica open tubular capillary columns having a conductive exterior coating and means for electrically coupling a power source to such coating, whereby it is now possible to effect direct resistive heating of the capillary column while controlling the temperature thereof. Such control is achieved by measurement of the resistance of the conductive coating, correlating such resistance with the temperature of the column and increasing or decreasing the electrical power supplied to such coating, as appropriate, to effect the desired adjustment in column temperature. Because of the low thermal mass of the column and the conductive coating, temperature changes can be effected readily thereby improving the speed of such separation and reducing the interval between resolution of successive samples. In the preferred embodiments of this invention, the system is incorporated in what is referred to as "short column" gas chromatography instrumentation and thus suitable for "non-selective" detection systems or selective detection methods. Because of the relative compact nature and low power demands of the system of this invention, such system can be operated as a portable unit.

2. Description of the Prior Art

The field of gas chromatography, as traditionally practiced, and as it has evolved more recently, involves five (5) basic, functionally interrelated components: (1) a carrier gas flow control system; (2) a low dead volume sample injection system (which allows for delivery of reproducible sample size); (3) a column oven that can be used for isothermal and temperature programmed analysis; (4) a low dead volume and high-sensitivity detector for high-speed gas chromatography and trace analysis; and (5) a short-time constant recorder or a chromatographic data recorder system for accurate recording of the peaks eluded from open tubular columns.

The design and operation of such equipment has as its ultimate objective the production of columns of extremely high resolving power for the separation of complex and difficult samples.

The control over column temperature is critical to the resolving efficiency of the column, whether the system is designed to operate isothermally or by temperature programmed analysis. Such column temperature control can be achieved by heating of the column in a convection oven or by resistance heating techniques. As has been appreciated, forced air heating of a column is relatively inefficient and temperature change of the column effected at a relatively slow rate. The application of direct resistance heating techniques to metal columns affords more rapid heating than forced air techniques, however, due to the relatively substantial thermal mass of such systems (both the metal columns and the ovens within which they are heated) such systems require a relatively long cool down (equilibration) periods. (See for example U.S. Pat. No. 4,096,908; column 2, lines 37-64).

Following separation or resolution of the mobile phase within the column, it is thereupon subjected to analysis by flame ionization techniques or by mass spectrometry. Where such analysis requires the transfer of the mobile phase from the column to the separate instrument (as in the case of mass spectrometry), heated transfer lines must be provided to maintain the mobile phase at a constant temperature. U.S. Pat. Nos. 4,650,964; 4,728,776; and 4,735,259 are representative of systems for transfer of a mobile phase from a column to an analytical instrument via a heated capillary tube. In each such system, the temperature of the mobile phase within the capillary tube is maintained at the appropriate temperature during the transfer process by means of what is referred to as a "heater tube".

Because of the obvious deficiencies in the above temperature maintenance and control systems, the search for alternative heating techniques continues. The direct resistance heating of metal-coated, thin-walled, flexible fused silica columns has been proposed because of the obvious advantages such a system would provide. Unfortunately, neither the manner of implementation of such a system, nor the feasibility of such system has been reported or established. Lee, Milton L. et al., *Open Tubular Column Chromatography* (A Wiley-Interscience Publication, John Wiley & Sons, 1984) Chapter 4, p. 110. While the above alternative to a more traditional technique of control of column temperature appears to offer promise, other potential problems are evident from this approach (i.e., temperature control). More specifically, even if thermocouples or resistance thermometers were available and small enough to accurately measure the temperature of these columns, the placement of the sensor against the column would create a local cold spot and lead to inaccurate temperature measurement. Thus, while the fused-silica column option appears attractive, there still remains numerous problems to overcome before such technology can be implemented successfully. Therefore, there continues to exist a need for improvement in the heating and temperature control of gas chromatography columns to permit rapid and efficient programmed temperature control and yet achieve such objectives without a prolonged equilibration period between successive analyses.

OBJECTS OF THE INVENTION

It is the object of this invention to remedy the above as well as the related deficiencies in the prior art.

More specifically, it is the principal object of this invention to provide a system and method for direct resistive heating and temperature control of open tubular capillary columns.

It is another object of this invention to provide a system and method for sensing of column temperature without use of external sensors.

It is still yet another object of this invention to provide a system and method for the rapid heating and cooling of chromatography columns to allow minimal delay between analysis of successful samples.

SUMMARY OF THE INVENTION

The above and related objects are achieved by providing a high resolution gas chromatograph comprising a fused silica open tubular capillary column having an essentially continuous conductive coating on its external wall which extends over the entire length of such column, means for injecting a sample into the inlet end of said capillary tube, means for injecting a carrier gas into the inlet end of the capillary tube, means for electrically coupling a source of electrical power to the continuous conductive coating of the capillary tube, and means for measuring the resistance of the electrically conductive coating and correlating such electrical resistance with the temperature of the column. This invention has the capability of providing direct resistive heating of fused silica open tubular capillary columns having a conductive exterior coating and means for electrically coupling a power source to such coating, whereby it is now possible to effect direct resistive heating of the capillary column while controlling the temperature thereof. Such control is achieved by measuring the resistance of the conductive coating, correlating such resistance with the temperature of the column and increasing or decreasing the electrical power supplied to such coating, as appropriate, to effect the desired adjustment in column temperature. Because the low thermal mass of the column and of the conductive coating, temperature changes can be effected readily thereby improving the speed of such separation and reducing the interval between resolution of successive samples. The phrase "low thermal mass" as used herein, and in the appended claims, is intended descriptive of the relative heat capacity of the conductive coating and/or the mass of the conductive coating per unit of volume of conductive material. In the context of this invention, low thermal mass is functionally defined in terms of the ability to detect and correlate changes in resistance of the conductive coating with temperatures of the column; and, the ability of the column to undergo rapid cycling in response to changes in temperature of the conductive coating. In the preferred embodiments of this invention, the system is incorporated in what is referred to as "short column" gas chromatography instrumentation and thus suitable for "non-selective" detection systems or selective detection methods. Because of the relatively compact nature and low power demands of the system of this invention, such system can be operated as a portable unit.

In the preferred embodiments of this invention, the column length is relatively short (on the order of two (2) to three (3) meters in length) as compared with thirty (30) meter column length found in conventional columns, thus, affording the ability to utilize this system with a relatively low power supply and rendering such system portable.

DESCRIPTION OF THE INVENTION INCLUDING PREFERRED EMBODIMENTS

Preliminary to a detailed discussion of the figures which are referenced herein, it will be helpful to briefly review the preferred environment of contemplated use and the various factors which effect design, operation and performance of high resolution gas chromatography. For purposes of illustration, the systems and methods of this invention are described within the context of short-column gas chromatography.

Short-column gas chromatography (SCGC) has become a popular analytical method for the rapid analysis of mixtures. SCGC applications employing non-selective detection systems (e.g. flame ionization detection) have been reported utilizing small diameter open tubular columns (<100 $\mu$m i.d.) for high-speed, high-resolution GC. When selective methods of detection are used, such as mass spectrometry (MS) and tandem mass spectrometry (MS/MS), high-resolution chromatographic separation is often not required. In fact, short columns combined with MS or MS/MS can often be used for extremely rapid analysis of targeted components in complex mixtures. The capability of analyzing thermally labile and/or polar compounds by SCGC (or GC/MS) has also added to the attractiveness of this method.

The speed of analysis in GC/MS and GC/MS/MS is determined by the time required by the chromatographic process. Moreover, in analyses where temperature programming is used, the rate at which samples can be analyzed is not only dependent on the time required by the separation, but also on the time required to equilibrate (cool) the column for the next injection of sample. There are two (2) approaches to solving this problem. One is not to program the temperature at all, but operate the column isothermally. However, this severely limits the range of compounds that can be analyzed in a single chromatogram. A second approach is to program the flow rate of the carrier gas instead of the temperature. Due to the high permeability of open tubular columns, the re-equilibration time is relatively short, but the range of boiling points of components separated using this technique is still not as wide as that obtainable with temperature programming. Since (in conventional systems) the column temperature is changed by changing the temperature of a large gas chromatograph oven, the rate at which a GC column can be heated or cooled in temperature-programmed GC is usually slow (typically 50° C./min or less depending on the manufacturer of the GC oven). In addition, chromatograph ovens are bulky and require large amounts of electrical power, and thus are not easily portable.

An alternative to the limitations described above is to heat the column directly instead of using a chromatograph oven. Recently, aluminum-clad fused silica open tubular (Al-clad FSOT) capillary tubes have become commercially available (SGE, Quadrex). These directly-heated tubes have been used by the inventors as simple transfer lines for introducing samples via GC into the collision cell of a triple quadruple mass spectrometer (report scheduled for publication in September, 1989). In this publication by the inventors, we describe in detail a method of heating these columns directly for temperature programming applications by passing an electrical current through the thin aluminum cladding coated on the outer surface of the column. A method of sensing the temperature of the Al-clad capillary directly, by measuring the column resistance instead of using external thermocouples or other temperature sensors, is also described.

The above concepts have been applied in the development of a compact GC probe, which resembles a conventional direct insertion probe, and interfaces with a commercially-available mass spectrometer. A GC probe utilizing packed columns operated isothermally has previously been described. The GC probe described here allows the temperature to be rapidly cycled for high-throughput GC/MS analyses. Removal or insertion of the probe from the mass spectrometer is through the normal probe inlet assembly. This facilitates changing of the column or allows rapid switch over to other techniques (e.g. solids probe, FAB, etc.) with minimal effort. Once the probe is removed from the mass spectrometer, the column can be rinsed with solvent without removing the column from the probe. This is attractive in cases when particularly "dirty" samples are being analyzed.

When a voltage is dropped across an Al-clad capillary, the column temperature increases depending on the amount of power dissipated. The power dissipated, P, is dependent on the current through the column, i, and the voltage across the column, V, according to equation (1).

$$P = iV \qquad (1)$$

The current is dependent on the voltage drop and the electrical resistance, R, according to equation (2).

$$i = V/R \qquad (2)$$

The electrical resistance is dependent on the length, diameter, and thickness of the Al coating on the outside of the capillary. The amount of heat required to increase the temperature of any substance by an increment $\Delta T$ is given by equation (3).

$$Q = mC\Delta T \qquad (3)$$

where Q is the heat (J or W−s), m is the mass of the material (g), C is the specific heat of the material (J/g °C), and $\Delta T$ is the change in temperature of the material (°C). From equation (3), it is apparent that objects of large mass require more heat or more power over a given time period to reach a given temperature. Al-clad FSOT GC columns are coated with a very thin aluminum film, and have a very small thermal mass. The low thermal mass of these columns allows them to be rapidly heated and cooled with much less electrical power than is normally required with chromatograph ovens. Since no large oven is needed, direct resistive heating is extremely attractive for use in portable GC instrumentation.

The low thermal mass of the Al-clad columns does present some problems if conventional methods are used to measure the column temperature. Currently, there are no thermocouples or resistance thermometers available that are small enough to accurately measure the temperature of these columns. Even if small sensors are used, placing the sensor against the column causes a local cold spot and leads to inaccurate temperature measurement. An alternative method of measuring the column temperature that avoids this problem is to use the column itself as the temperature sensor. The resistance of any metallic conductor is linearly related to its temperature over a wide temperature range and is given by equation (4).

$$R_T = R_o(1 + \alpha T) \qquad (4)$$

where $R_T$ is the resistance (Ω) at temperature T (°C), $R_o$ is the resistance at 0° C., and $\alpha$ is the temperature coefficient of resistivity of the metal (°C.-1). In fact, equation (4) is the basis of operation of Pt resistance thermometers, which are widely used in scientific applications. The resistance of a column is readily calculated during resistive heating if the current through the column and the voltage across the column are measured. Once a calibration of temperature versus resistance has been performed, a determination of the column resistance can be used as a direct measure of the column temperature.

PREFERRED EMBODIMENTS

A Finnigan MAT TSQ70 triple quadruple mass spectrometer was used for this work. The instrument was tuned with FC43 (perfluorotributylamine) with the GC probe in place. The same removable ion volumes used with the direct insertion probe were used with the GC probe. The electron multiplier was maintained at 1000 V and the preamplifier gain was set at $10^8$ V/A. Electron ionization (EI) with an electron energy of 70 eV was used; normal Q1 mass spectra were acquired for all MS experiments.

Wide-bore (0.53 mm i.d.) Al-clad FSOT columns with a non-polar 1.0 μm film BP-1 stationary phase (SGE) were used with the GC probe. Wide-bore columns may be about three (3) to five (5) meters long and have an inside diameter of about 0.5 to 0.6 millimeters. Narrow-bore columns (0.33 mm i.d., 0.5 μm film, BP-5 stationary phase) were also evaluated for use in the GC probe; however, for all chromatograms reported here, wide-bore columns were used, which allowed for a mechanically simple injection port. Narrow-bore columns may be about three (3) to five (5) meters long and have an inside diameter of about 0.3 to 0.4 millimeters.

Electronics for Column Heating

Figure 1:
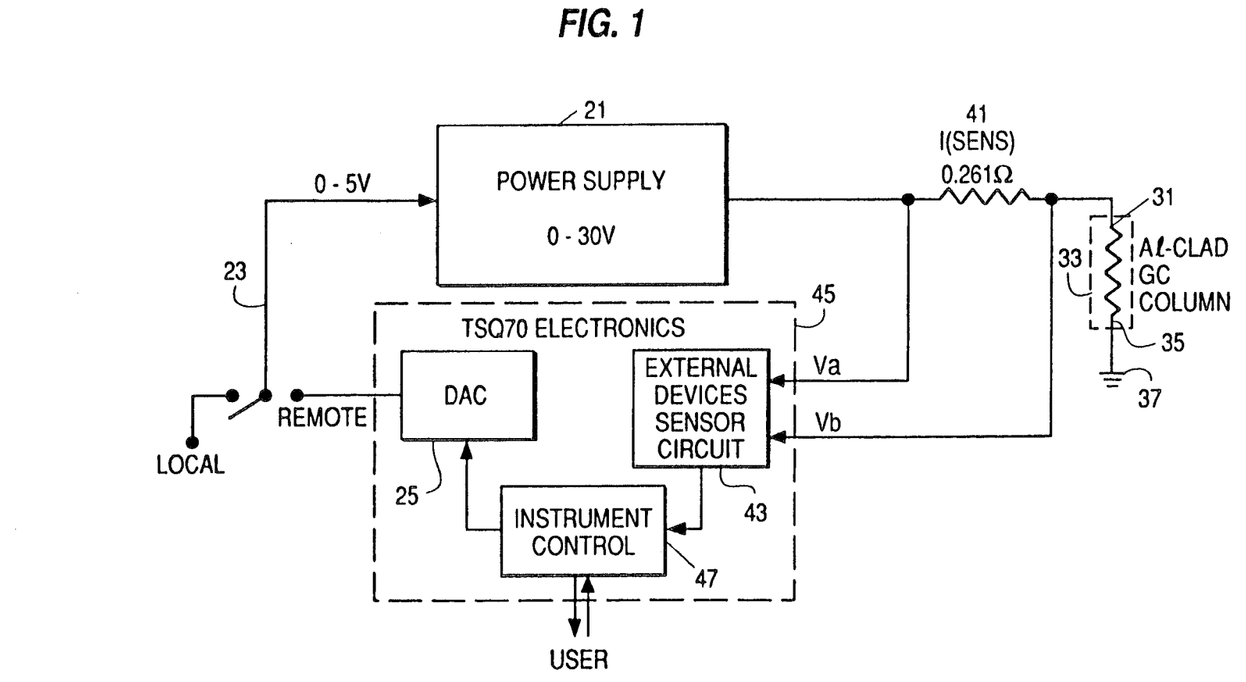
FIG. 1 is a schematic diagram of electronics used for resistive heating and temperature sensing of metal-clad capillary columns.

A programmable DC power supply was constructed in-house and was used to control the voltage across the Al-clad GC columns. The electronic components for the power supply are contained in a box which is approximately 10 in. × 6 in. × 3.5 in. A schematic diagram of the overall system electronics including a DC power supply (21) is shown in FIG. 1, with electronic circuitry of the DC power supply (21) being illustrated in FIG. 2. The output of the power supply (21) (up to 30 V) is controlled through a control lead (23) by an input control voltage of 0–5 V DC. The control voltage can be varied by a ten-turn potentiometer (not shown) on the front of the control of external devices. One of these user outputs was used to generate a control voltage for the power supply. The control voltage (from the potentiometer or a DAC (25)) is fed into a voltage follower with variable gain. The output of the op-amp (27) provides a bias to the base of a power transistor (29) that determines the output voltage of the power supply (21). The output of the power transistor (29) which is rated at 30 V and 30 A is supplied to one end (31) of the aluminum cladding on a GC column (33). The other end (35) of the aluminum cladding is connected to ground (37). In the present configuration the output of the lower supply (21) is limited by the transformer (39), which is rated at approximately 6 A. Typically, the gain of the voltage follower is set such that the power supply (21) yields the maximum desired temperature at the maximum control voltage. This versatility is important, since a change in the length or diameter of the column (33) changes the amount of power required for the column (33) to reach a particular temperature. No additional circuitry had to be designed to measure the column voltages and currents. The voltage drop across the column (33), as well as the voltage drop across a 0.261 Ω current sensing resistor (41) connected between the one end (31) of the aluminum cladding and output of the power supply (21) were measured with an external device sensor circuit (43) already present in the TSQ70 electronics (45). This circuit (43) consists of five (5) differential amplifiers, an analog multiplexer, and an analog-to-digital converter (ADC). The voltages to be determined were fed into two (2) separate differential amplifiers of the sensor circuit. This allows the voltages to be displayed and/or plotted in real time with the computer-controlled TSQ70 electronics (45) and the Instrument Control Language (ICL) in an instrument control (47). Programs were written in ICL that allowed the voltage across the column (33) to be increased linearly with time during the acquisition of data. The linear voltage ramp was used to simulate the linear temperature ramp commonly used in temperature programming. However, it should be pointed out that any desired voltage ramp could be created with this system (e.g. exponential, logarithmic, etc.), by a simple modification of the ICL program.

Temperature Sensing

Figure 2:
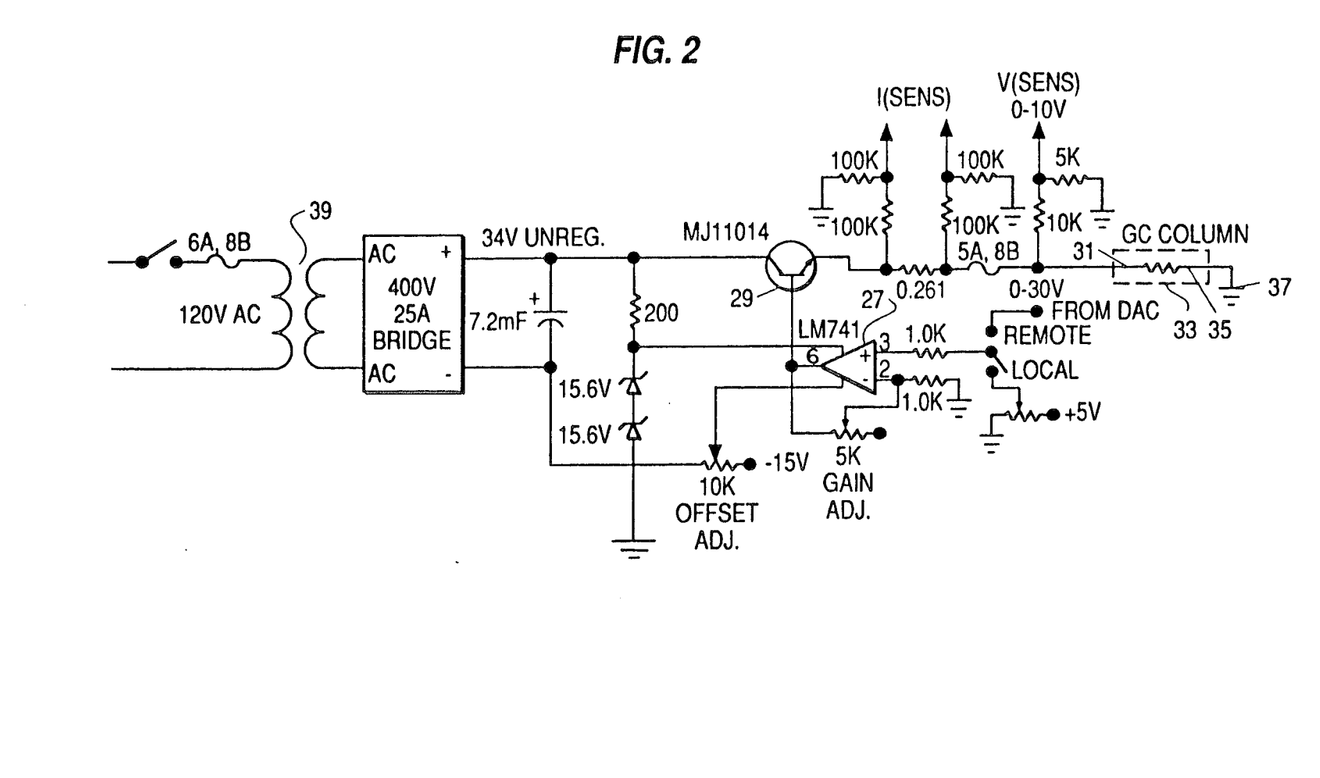
FIG. 2 is a circuit diagram of programmable 30 V DC power supply designed for column heating.

The electrical resistance of the aluminum cladding of the column (33), obtained by measurement of the voltage and current, was used as an indication of the column temperature. Al-clad GC columns (33) were "calibrated" by placing them in a GC oven (Varian model 3400) and recording the resistances of the columns as a function of GC oven temperature. A wide-bore Al-clad FSOT column (0.53 mm i.d. × 3.14 m), and two (2) different lengths (4.77 m and 3.05 m) cut from the same narrow-bore (0.33 mm i.d.) Al-clad FSOT column were calibrated using this method. The nominal resistances of these columns were very low (ca. 0.9 Ω/m for the narrow-bore column and 0.5 Ω/m for the wide-bore columns), and thus were too small to be accurately and precisely measured with a typical digital multimeter (DMM). In order to obtain accurate resistance measurements for the calibration, the DC power supply was used to apply a small voltage drop (e.g. 50 mV) (33) cross the column as shown in FIGS. 1 and 2. The current through the column and the voltage drop across the column were measured with two (2) DMMs (Fluke model 75). The resistances were then calculated from the voltages and currents measured. The voltages applied during calibration were not high enough to cause a significant amount of column heating.

GC Probe Design

Figure 3:
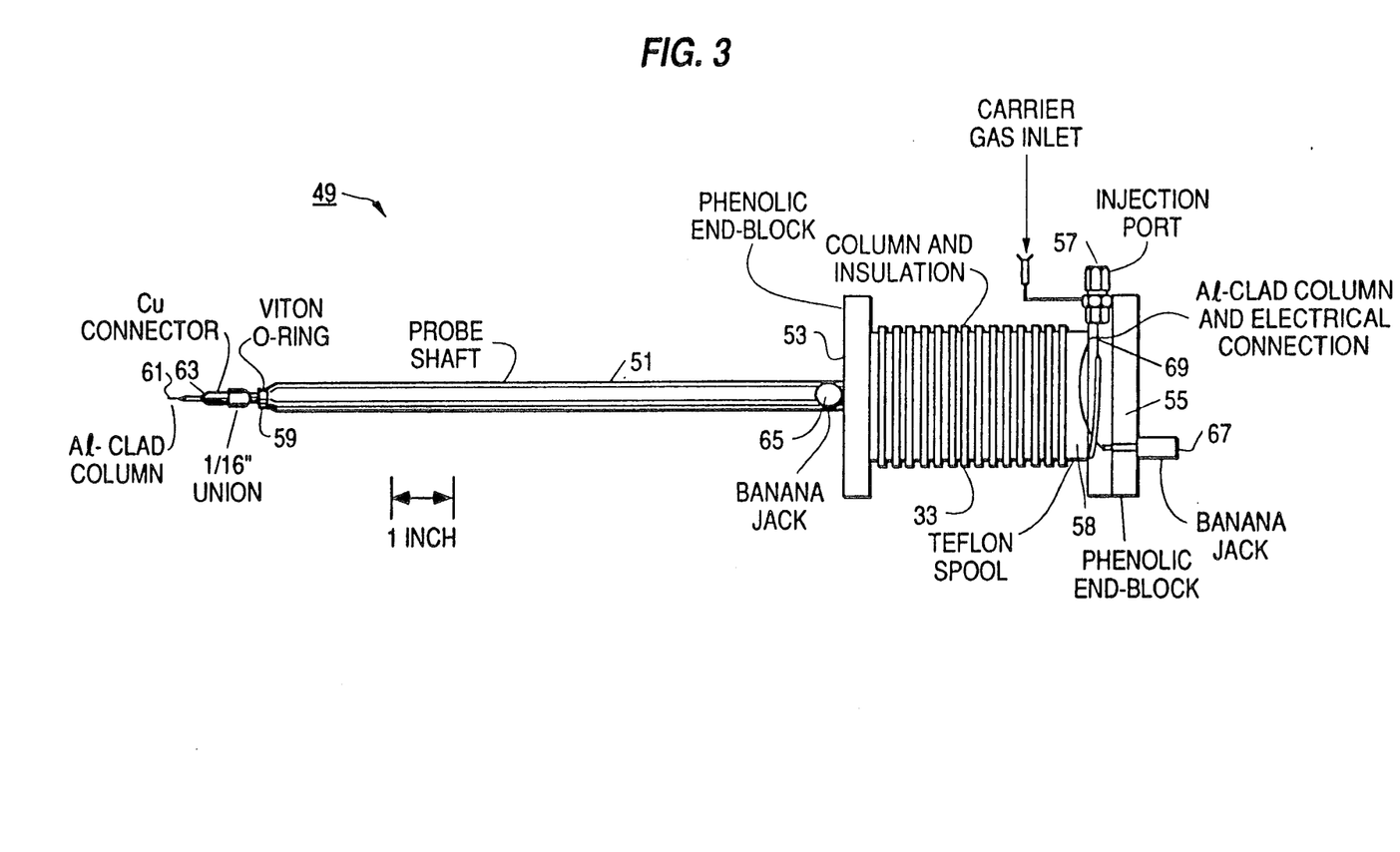
FIG. 3 is an illustration of direct insertion gas chromatograph probe.

The GC probe (49) is schematically illustrated in FIG. 3. The 1.27 cm × 28 cm stainless steel probe shaft (51) was adapted from a Finnigan 4500 series ion volume insertion/removal tool. The probe shaft (51) is threaded and screwed into one endblock (53) of the two four (4) inch square end-blocks (53 and 55) (machined from phenolic material). The injection port (57) is positioned in a milled slot on the other end-block (55) and is held firmly in place by a set screw (not shown). The column (33) was wrapped around a 2.5 inch diameter Teflon spool (58). The column (33) is covered with Nextel glass braid insulation (Omega Engineering) which is also is coiled around the Teflon spool (58). The spool (58) is held between the two (2) end-blocks (53 and 55) and contains a slot (not shown) that allows the column (33) to be inserted through the spool and down the length of the probe shaft (51). The 1/16 inch stainless steel union (Swagelok) with a graphitised vespel ferrule and a Viton o-ring (59) are used to form a vacuum-tight seal at the distal end of the probe shaft (51). Approximately two centimeters (2 cm) of the column extends from the end of Swagelok union, as indicated by (61). A copper connector (63) slides over these last few centimeters of the column (33) and electrically connects the end of the column (63) to the probe shaft. Electrical leads from the DC power supply plug into the banana jacks (65 and 67) mounted on the probe assembly. It is very important to minimize the contact resistance of the electrical connections to the column (33), since poor connections result in power consumption and local heating at the point of contact. In addition, large connectors have a large thermal mass and dissipate heat near the contact. For these reasons, the electrical connection to the head of the column (69) was made with a small removable clip lead (not shown). The probe shaft (51), which is used as a ground return, remains cool during column heating, since the resistance of the probe is much less than that of the columns used. The nominal resistance of the column in the probe was always checked prior to applying power to insure good electrical connections. The GC probe shaft is inserted through the probe inlet assembly and the end of the probe fits firmly against the ion volume contained in the ion source block.

A compact, low thermal mass injection port (57) was fabricated from a ⅛ in. × 1/16 in. stainless steel tube reducing union (Swagelok). For the introduction of carrier gas into the injection port (57), a hole was drilled into the side of this fitting and a 1/16 inch o.d. stainless steel tube was silver-soldered in place. The wide-bore column is inserted into the smaller end of the union and is sealed with a nut and a graphitised vespel ferrule. The top of the injection port contains an ⅛ inch nut and a septum. A standard GC syringe (SGE), equipped with a 26-gauge needle (not shown), was used to inject samples directly onto the wide-bore columns. The inside of the injection port contains a stainless steel guide, which directs the syringe needle to the column entrance. Upon injection, the syringe needle enters the column and is inserted far enough that the sample is injected past the point where the electrical connection is made. This minimizes sample loss due to unvolatilized components. The injection port (57) remains cold when the column is heated, and thus does not have to be cooled between injections.

FLOW CONTROL SYSTEM

Since short wide-bore columns (typically 3 m in length) were used, the injection port (57) could not be operated at conventional injection port pressures (i.e. atmospheric pressure and above) without a carrier gas flow rate exceeding the normal operating pressure of the mass spectrometer. Instead, the injection port was maintained at lower pressures (typically 100-200 torr) with a flow control system described elsewhere. This system utilizes a mass flow control system (MKS model 1159A flow controller and model 246 readout) instead of a pressure regulator to regulate the flow of carrier gas to the column. The use of sub-atmospheric inlet pressures did require some consideration of injection technique, since it was possible for the sample to be prematurely aspirated from the syringe by the vacuum in the injection port. It was found that the best way to avoid this problem was to use a gas-tight syringe and to draw the sample as well as a small volume (e.g. 1 $\mu$L) of air into the syringe barrel.

The volumetric flow rate of He carrier gas used with the sub-ambient inlet pressures was typically 3.5 ml/min. Flow rates were determined by measuring the flow output of the flow controller with a soap bubble meter prior to connecting the carrier gas line to the injection port. Davies has shown that, under the conditions of vacuum outlet, flow rates can be calculated by equation (5).

$$Q = 64\pi nL^3/9t_o^2 \quad (5)$$

where Q is the flow rate reduced to atmospheric pressure (mL atm s$^{-1}$), $t_o$ is the retention time of the unretained air peak (s), n is the gas viscosity (poise), and L is the column length (m). However, when short columns are used, the air peak times are very short and are not easily measured. For example, a three meter (3 m) column operated at a typical gas velocity of 300 cm/s has an air peak time of 1 s; therefore, in these experiments it was more convenient to measure flow rates instead. Given that the average gas velocity is $$v = L/t_o \quad (6)$$

Once the flow rate is known, $v$ can be calculated if equation 6 is substituted into equation 5 yielding $$v = (375Q/16\pi nL)^{\frac{1}{2}} \quad (7)$$

where Q is in mL atm min$^{-1}$, L is in m, n is in poise, and $v$ is in cm/s. The inlet pressure (P$_i$, dynes/cm$^2$) can be calculated from the Poisuelle equation for vacuum outlet conditions.

$$P_i = 32vnL/3r^2 \quad (8)$$

where r is the column radius in cm, and L is in cm. At the flow rate of 3.5 mL/min of He at 25° C., the gas velocity was calculated to be ca. 204 cm/s with an inlet pressure of 146 torr.

RESULTS AND DISCUSSION

Calibration of Columns for Temperature Sensing

Figure 4:
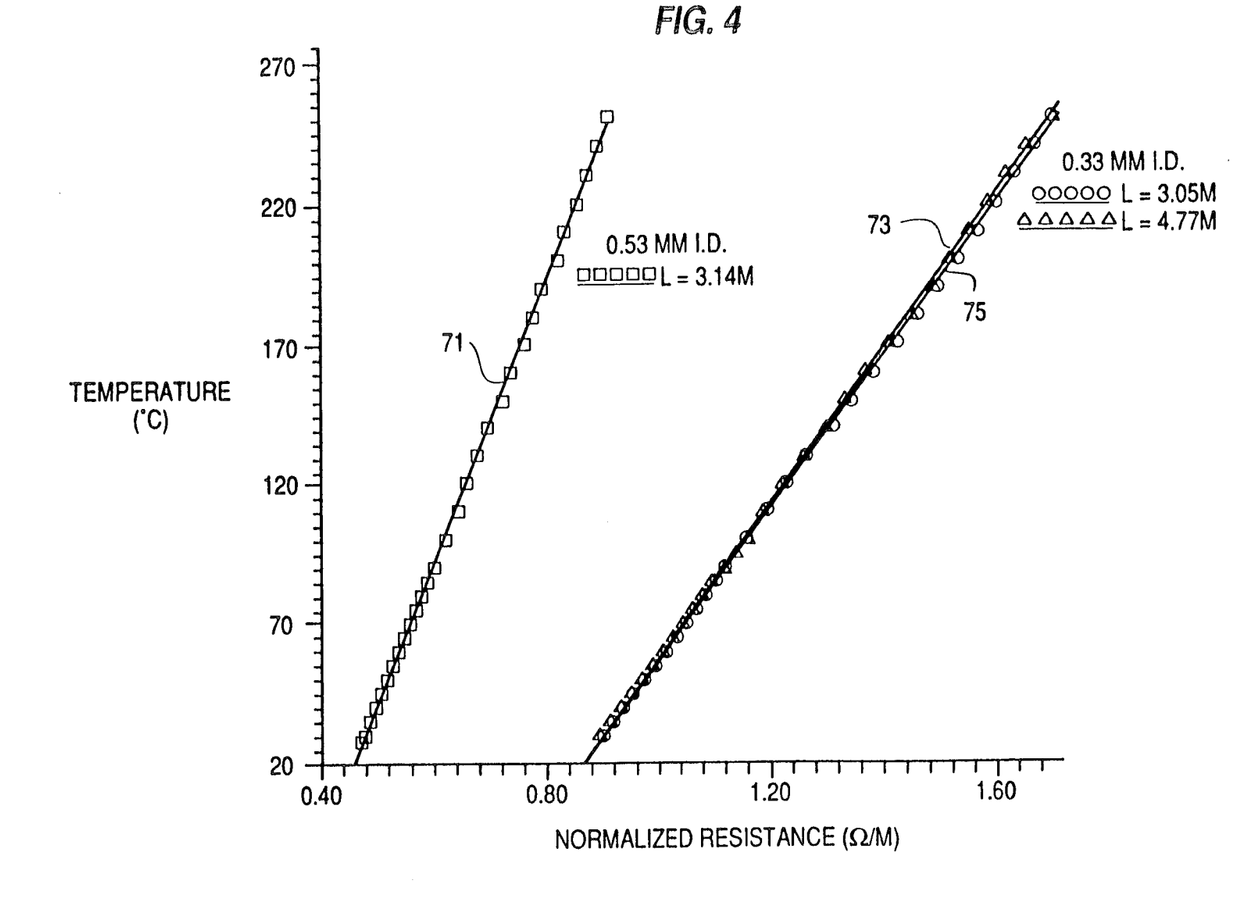
FIG. 4 is a calibration of column temperature versus normalized resistance ($\Omega$/m) for two (2) different diameter metal-clad capillary columns. The temperature of a resistively-heated column could be determined from the calibration line with knowledge of the column resistance and the length.

Data obtained for the calibration of the column resistance versus temperature are shown in FIG. 4. The column resistances were normalized by dividing by the length of the column used in the calibration. Length normalization was necessary, since the same length of column was not always used in the GC probe. Once the calibrations were performed, the temperature of a resistively-heated column could be determined from the relationship $$T = aR/L + b \quad (9)$$

where T is temperature (°C.), R is the resistance ($\Omega$), L is the column length (m), and a and b are the slope and y-intercept of the linear calibration curve, respectively. The slopes, y-intercepts, and standard deviations from the linear lease squares fits of the calibration data are shown in Table 1. As shown in FIG. 4 and Table 1, essentially the same calibrations were obtained for the two (2) different lengths of the narrow-bore column. A first curve (71) is for a column with a 0.53 mm i.d. and a 3.14 meter length. A second curve (73) is for a column with a 0.33 mm i.d. and a 3.05 meter length. A third curve (75) is for a column with a 0.33 mm i.d. and a 4.77 meter length. This is an indication of the uniform thickness of the Al coating. Since these columns were cut form the same original column, no generalizations can be made about the column-to-column uniformity. As shown in FIG. 4, the resistance of the wide-bore column is less than that of the narrow-bore column. This is due to the fact that there is a greater mass of Al per unit length on the wide-bore column, which can be attibuted to the greater surface area and/or thicker Al cladding on the wide-bore column. Note that the y-intercepts obtained were practically the same regardless of the column diameter. This can better understood by a rearrangement of equation (4), as shown in equation (10):

$$T = R_T/aR_o - 1/a \quad (10)$$

which demonstrates that the y-intercept (1/a) is independent only on the temperature coefficient of resistivity ($\alpha$), a fundamental property of the metal. Due to the limited availability of these columns, it has not yet been possible to compare calibrations from different columns of the same diameter. If the column-to-column Al coating thicknesses were consistent, then calibrations would not have to be repeated for each one column. Rather, the calibrations would only need to be done for each new diameter column that was used.

Since the resistance of the column, R, is the voltage across the column, V, divided by the current along the column, i:

$$R = V/i$$

Then equation 10 can be expressed in terms of the measured voltage and currents:

$$T = \frac{V_T/i_T}{\delta V_o/i_o} - \frac{1}{\delta}$$

Wherein
$V_T$ = measured voltage at T
$i_T$ = measured current at temperature T
$V_0$ = measured voltage at 0° C.
$I_0$ = measured current at @ 0° C.
$c$ = temperature coefficient of resistivity of coating
$V_T$ and $V_o$ are the measured voltages.
T is the column temperature.

One advantage of this method of direct column temperature sensing, since thermocouples or other temperature sensors are not needed, is the simplicity of the electronic circuitry required. This could be an important advantage in the design of portable instrumentation for environmental or process monitoring. Another advantage that is particularly important in this application is that measurement of the column resistance is effectively a length-average temperature measurement. The temperature measured at each point along the column may vary, depending on the insulation and thickness of the Al coating at a particular spot; thus, measurement of the column temperature at one of these spots may not be an accurate representation of the average column temperature. In addition, we have observed that temperature sensing by conventional means (e.g. with a thermocouple placed in contact with the column) causes the temperature of the column to drop near the point of measurement and leads to inaccurate determinations. This direct measurement of column temperature, might be attractive for other applications as well. For example, it is normally assumed that the temperature of a column inside an oven directly follows the oven temperature; this method could be used to directly measure the actual temperature of an Al-clad GC column inside a chromatograph oven.

Temperature response characteristics

Figure 5:
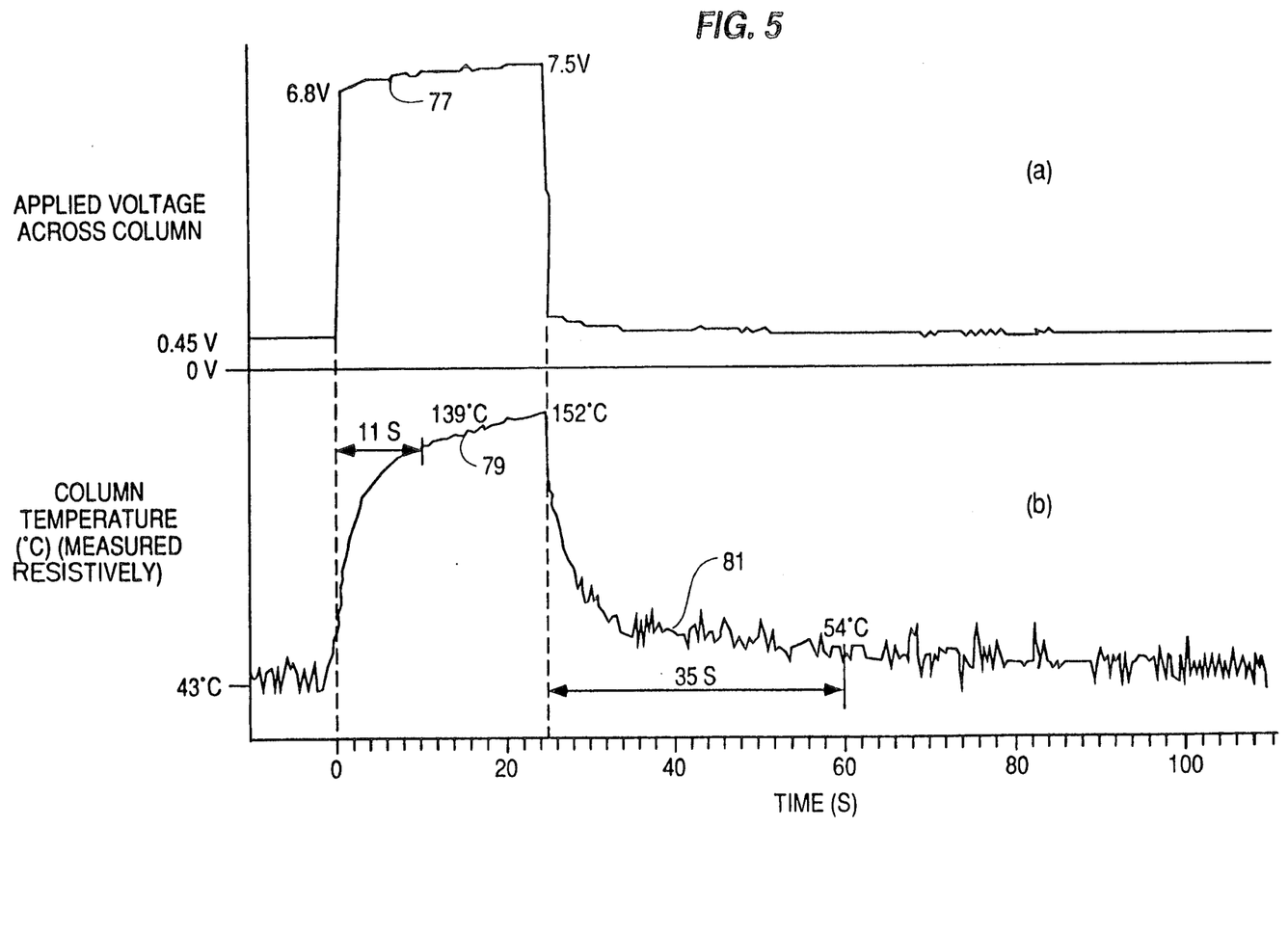
FIG. 5 is a response characteristic for a resistively-heated 2.3 m $\times$ 0.53 mm i.d. Al-clad FSOT (aluminum-clad, fused silica, open tubular) column during a 25 second heating period: (a) applied voltage across the column, and (b) indicated temperature obtained from column resistance measurement.

As mentioned previously, direct resistive heating of Al-clad columns allows for extremely rapid cycling of the column temperature due to their extremely low thermal mass. The applied voltage curve (77) and the column temperature curve (79) of FIG. 5 show the temperature response of a 2.3 m × 0.53 mm i.d. Al-clad FSOT column installed in the GC probe, after the voltage output of the transistor of the power supply had been stepped from 0.5 V to 8.2 V and then returned to 0.5 V after a period of 25 s. Note that the voltage across the column (FIG. 5(a)) did not remain constant during the heating period, but increased from 6.8 V to 7.5 V. Similarly, the column voltage did not instantaneously return to its initial value of 9.45 V at the end of the heating cycle. The slow response of the column voltage can be attributed to an increase in the column resistance as the temperature is increased. The output voltage of the transistor and the resistance of the 0.261 Ω resistor remain constant during the heating period; thus, as the column resistance increases, a greater fraction of the transistor output voltage is dropped across the column. This causes the column voltage to slowly increase during heating and slowly decrease during cooling.

During the 25 s heating cycle, the column temperature increased from 43° C. to 150° C. During the first second of the 25 s heating period, the column temperature increased from 43° C. to 83° C., which represents an initial heating rate of 40° C./s or 2400° C./min. The heating and cooling response of the column exhibits an exponential behavior, much like that caused by impedance in an electrical circuit. However, the response times for heating and cooling are not the same. In this example, the heating response time of the column is defined as the time required to raise the column temperature ninety percent (90%) of the way from 43° C. to 150° C. (i.e., to 139° C.). As shown by the curve (79) in FIG. 5, this response time was found to be approximately 11 s. The temperature increase from 43° C. to 139° C. in 11 s represents an average rate of increase of 8.7° C./s or 524° C./min. For comparison, the ballistic heating rate of a typical gas chromatograph oven from 50° C. to 150° C. is only about 50° C./min. In addition, the maximum heating rate for a typical on-column injector is only 150° C./min. Obviously, the method of direct resistive heating offers considerable improvement in terms of rapidity of response when compared to oven heating.

In applications where extremely rapid temperature ramps are used (as in the example shown above), the speed of repetitive analyses will most likely be limited by the time required to re-equilibrate (cool) the column temperature between injections. During the first second of cooling, the column temperature dropped from 152° C. to 112° C., which is an initial cooling rate of 40° C./s or 2400° C./min. Note that the initial heating and cooling rates are the same. The response time for cooling the column, defined as the time required to cool the column ninety percent (90%) of the way back down to 43° C. from 150° C. (i.e., to 54° C.), was determined to be approximately 35 s. as shown by the cooling segment (81) of the curve (79). This represents an average rate of cooling of 2.7° C./s or 165° C./min. For comparison, the temperature cool-down time for a typical gas chromatograph oven over the same temperature range would be approximately four (4) minutes (about seven (7) times longer).

As shown in FIG. 5, there is some thermal lag associated with the heating and cooling of these columns. A small amount of thermal lag can be attributed to the voltage regulation of the power supply. Referring to FIG. 2, the power supply regulates the voltage output of the transistor (29); thus, the voltage across the column (33) changes as the temperature (and hence the resistance) of the column changes. Much of this thermal lag can be attributed to the slow thermal response of the insulation that was used to electrically isolate the column (33); thus, it is expected that these columns would exhibit even faster thermal response if the glass braid insulation were eliminated. This would be possible if the column could be wrapped around a grooved spool, which would separate each strand of the column and prevent electrical shorting. Nevertheless, even without any further improvements, the temperature response characteristics are impressive when compared to conventional GC ovens.

Another advantage of direct column heating is that very little electrical power (or energy) is needed. For example, approximately 35 W of electrical power applied for 25 s (0.875 kJ of energy) was required to resistively heat the 2.3 m column to 150° C. For comparison, a typical GC oven utilizes a 2400 W heater (240 V AC, 10 A). Assuming an average ballistic heating rate of 50° C./min, three (3) minutes would be required to heat the oven from 50° C. to 150° C. Approximately 432 kJ of energy would be consumed, which is nearly 500 times more energy than that required by direct resistive heating. In addition, a typical injector is heated separately from the oven and requires an additional 100-300 W of power. When the entire column is heated resistively and on-column injection is used, as is the case with the GC probe, no additional injector heaters are required. The power required to resistively heat a column to a particular temperature is dependent on the thermal mass of the column (equation 3). For columns of the same diameter and Al coating thickness, the power needed to reach a particular temperature is directly proportional to the column length. For example, a 23 m column would require ten (10) times more power than the 2.3 m column, or 350 W, to reach 150° C.

One limitation of the present system is that the voltages sensed at the lower column temperatures are too small to yield a high degree of precision for the column resistance (and hence temperature) measurement. This is the reason for the quantization noise (at low voltages and temperatures) in the temperature profile of FIG. 5. This limitation could be remedied if an autoranging circuit was used to automatically adjust the sensitivity of the resistance-sensing electronics.

Performance of GC probe

Figure 6A:
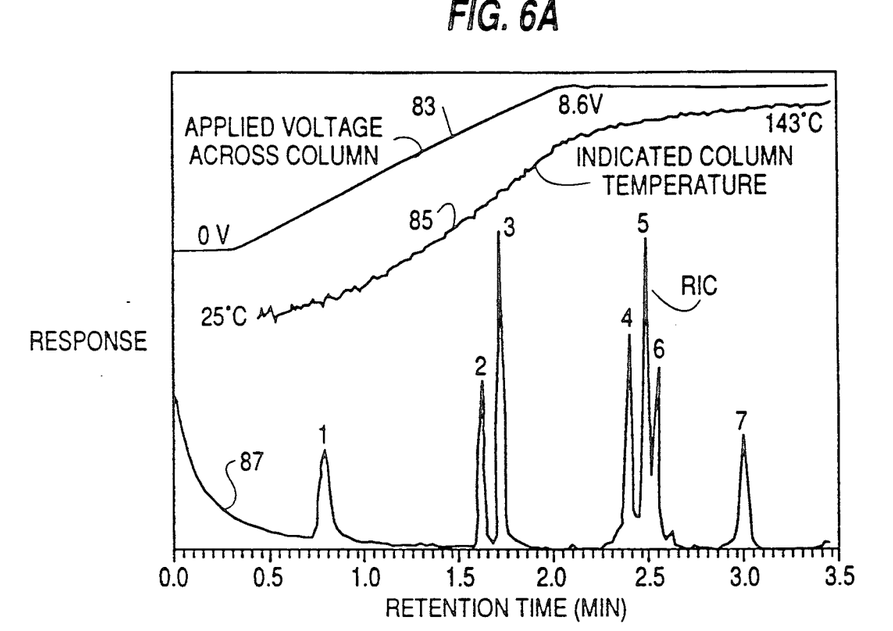
FIGS. 6A and 6B are reconstructed ion chromatograms obtained with the GC (gas chromatograph) probe of FIG. 3 using a 3.19 m $\times$ 0.53 mm i.d. column and two (2) different linear column voltage programs. (A) final voltage of 8.6 V after two (2) minutes, (B) final voltage of 10.8 V after one (1) minute. The components of the mixture are: 1,2-chlorophenol; 2,2,4-dimethylaniline; 3, n-undecane; 4,1-undecanol; 5, acenaphthylene; 6, tetradecane; 7, pentadecane.
Figure 6B:
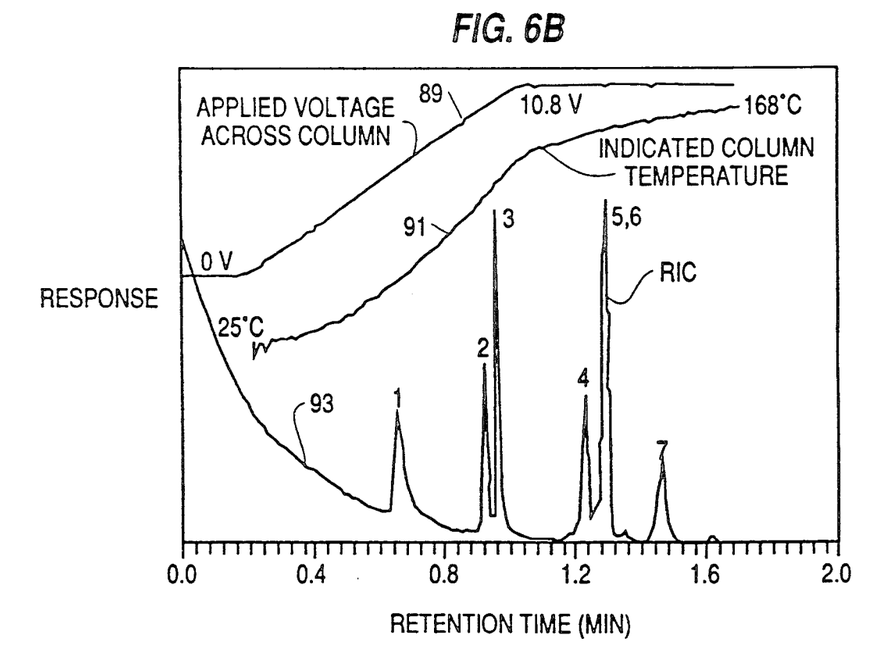

FIGS. 6(A) and 6(B) illustrate two (2) different RIC (reconstructed ion chromatograms) that were obtained with the GC probe and two (2) different temperature ramps using a 3.19 m×0.53 mm i.d. Al-clad FSOT column. A 0.5 μL on-column injection was made in both cases. The concentration of each component (identified in the figure) was 250 ng/μL in hexane. In FIG. 6A, the voltage shown by the curve (83) across the column was programmed, after a delay of 15 s, from 0 V (25° C.) to 8.6 V in two (2) minutes to produce the temperature rise shown by the curve (85). The voltage was held constant for another 1.5 minutes, resulting in a final temperature of 143° C. In FIG. 6B, as shown by the curve (89), the same initial voltage (temperature) was used as in FIG. 6A to produce the temperature rise shown by the curve (91). The delay was 10 s and the final voltage was 10.8 V after one (1) minute. The voltage was held constant at 10.8 V for an additional 30 s, resulting in a final temperature of 168° C.

The RIC in FIG. 6A is shown by the curve (87). The RIC in FIG. 6B is shown by the curve (93). On average, the peak widths at fifty percent (50%) height are approximately 3 s in FIG. 6A and 2 s in FIG. 6B. The earliest eluting peak (2-chlorophenol) has a larger peak width in both cases. This can be attributed to the deleterious effects of the solvent. During cold on-column injection, components that are much less volatile than the solvent are focused at the head of the column and exhibit very narrow band widths. In contrast, the volatile, early eluting components (if not well separated from the solvent front) can partition in the liquid solvent as well, resulting in increased solid peak widths. This problem can often be avoided if smaller volumes of solvent are injected, or more reliably, if cryofocusing is used to trap the solutes in a narrow band at the head of the column. The peak widths obtained here are extremely narrow considering that the column that was used had a stationary phase film that is normally considered thick (1.0 μm). In addition to increasing the chromatographic resolution, the capability of obtaining narrow band widths increases the sensitivity and lowers the limit of detection.

In another study, the reproducibility of retention times and peak areas obtainable with the GC probe were measured. The retention times and resulting integrated peak areas were measured for four (4) on-column, temperature-programmed injections of 150 ng tetradecane on a 3.3 m×0.53 mm i.d. column. Tetradecane, which has a boiling point of 232° C. had a retention time of 90.00±0.81 s (relative standard deviation (RSD) of 0.9%). The integrated peak area of the m/z 198 molecular ion of tetradecane was determined with a precision of 3.5% RSD, which is certainly within the limits of error for injections performed with a standard syringe.

The concept of resistively heating Al-clad FSOT columns has been successfully demonstrated by this invention. The direct method of column heating obviates the need for a large chromatograph oven, and should be widely applicable in portable, low-power gas chromatographic instrumentation. This was demonstrated with the design of a compact GC probe for high-throughput analyses in GC/MS and GC/MS/MS. Measurement of the column resistance was shown to be a simple yet accurate method of directly sensing the temperature of low thermal mass Al-clad columns. It was also demonstrated that linear voltage programming of the Al-clad columns can be used to approximate linear temperature programming. Future application of proportional-integral-differential (PID) feedback control of the column temperature and elimination of the column insulation is expected to further improve the thermal response characteristics of direct resistive heating of these columns. Accordingly, the foregoing description of some of the preferred embodiments is not intended as delineating the scope of protection, which is reserved to allowed claims.

What is claimed is:

1. In a gas chromatography method comprising the steps of providing a tubular non-metallic column, heating said column according to a predetermined program, passing a mixture of chemical components into the inlet end of said column whereby said components are selectively separated in said column, and detecting said separated components as they emerge from the outlet end of said column, the improvement consisting essentially of:
   a. providing a tubular non-metallic column of low thermal mass having a continuous electrically resistive film adhered to the outside surface of, and over substantially the entire length of, said column; and
   b. passing a controlled electric current through said film so as to directly heat said column in a controlled manner, wherein said controlled heating of said column includes:
      (i) calibrating said electrically resistive film so as to derive a set of values that relate the resistance of said film to the temperature thereof;
      (ii) measuring the voltage applied to said resistive film and the current passing therethrough at each pre-selected point in time; and
      (iii) deriving the temperature of said film at each said point in time by applying the formula:
      wherein:
      T = column temperature;
      $V_T$ = measured voltage at T;
      $i_T$ = measured current at T;
      $V_o$ = measured voltage at 0° C.;
      $i_o$ = measured current at 0° C.;
      δ = temperature coefficient of resistivity of film.

2. The method defined in claim 1 wherein said column consists essentially of fused silica and said resistive film is selected from the group consisting of aluminum, aluminum oxides and mixtures thereof.

3. The method defined in claim 2 wherein said column is about three to about five meters long and has an inside diameter of about 0.3 to about 0.4 millimeters.

4. The method defined in claim 2 wherein said column is about three to about five meters long and has an inside diameter of about 0.5 to about 0.6 millimeters.

5. The method defined in claim 1 including, in step (b), electrically grounding said resistive film at a ground connection point near one end of said column, connecting a source of electric power to said film at a power connection point near the other end of said film, and passing said electric current through said film between said connection points.

6. In a gas chromatograph comprising a tubular nonmetallic column, means for introducing a mixture of chemical components into the inlet end of said column, means for detecting separated components of said mixture emerging from the outlet end of said column, and means for controllably heating said column, the improvement comprising a continuous resistive film adhered to the outside surface of, and over substantially the entire length of, said column, means for passing a controlled electric current through said film so as to directly heat said column in a controlled manner, and means for measuring the resistance of said film while passing said controlled electric current therethrough.

7. The gas chromatograph according to claim 6 wherein the resistive film is of variable thickness so as to create at least two discrete zones along the length of the column wherever the resistance of one discrete zone is greater than another discrete zone, and the temperature within each discrete zone varies with the resistance of the resistive film in each such zone.

8. The gas chromatograph according to claim 7 wherein the temperature of each discrete zone is independently controlled.

9. The gas chromatograph according to claim 8 wherein the temperature of the discrete zone of the column toward the inlet end is maintained at a lower temperature than the discrete zone toward the outlet end of the column.

10. The gas chromatograph according to claim 6 wherein said means for passing an electric current includes a first electrical connector to said resistive film near one end of said column and a second electrical connector to said resistive film near the other end of said column.

11. The gas chromatograph according to claim 10 wherein said first electrical connector is connected to a source of electric power and said second electrical connector is connected to an electrical ground.

12. The gas chromatograph according to claim 10 wherein said measuring means includes means for determining the voltage across, and the current passing through, said film between said electrical connectors.

13. The gas chromatograph according to claim 6 wherein said column consists essentially of fused silica and said resistive film is selected from the group consisting of aluminum, aluminum oxides and mixtures thereof.

14. The gas chromatograph according to claim 13 wherein said column is about three to about five meters long and has an inside diameter of about 0.3 to about 0.4 millimeters.

15. The gas chromatograph according to claim 13 wherein said column is about three to about five meters long and has an inside diameter of about 0.5 to about 0.6 millimeters.

* * * * *

UNITED STATES PATENT AND TRADEMARK OFFICE
CERTIFICATE OF CORRECTION

PATENT NO. :     5,114,439
DATED      :     May 19, 1992
INVENTOR(S) :    Richard A. YOST, ET AL It is certified that error appears in the above-identified patent and that said Letters Patent is hereby corrected as shown below:

In column 14, at line 55 (Claim 1, line 25), insert the following formula:

-- 
$$T = \frac{V_T/i_T}{\delta\, V_o/i_o} - \frac{1}{\delta}$$
--

Signed and Sealed this

Thirteenth Day of July, 1993

Attest:

MICHAEL K. KIRK

*Attesting Officer*        *Acting Commissioner of Patents and Trademarks*

UNITED STATES PATENT AND TRADEMARK OFFICE
CERTIFICATE OF CORRECTION

PATENT NO. :    5,114,439
DATED      :    May 19, 1992
INVENTOR(S) :   Richard A. YOST, ET AL It is certified that error appears in the above-identified patent and that said Letters Patent is hereby corrected as shown below:

Title Item (54): under the title of the invention, please add the following:

--    Research leading to the completion and reduction to practice of the invention was supported, in part, by the Department of the Army. Accordingly, the invention may be manufactured, used and licensed by or for the Government of the United States for Governmental purposes without payment of any royalties thereon. --

Signed and Sealed this

Eleventh Day of January, 1994

Attest:

BRUCE LEHMAN

Attesting Officer

Commissioner of Patents and Trademarks